US00RE43134E

(19) United States
(12) Reissued Patent
Wadia et al.

(10) Patent Number: US RE43,134 E
(45) Date of Reissued Patent: Jan. 24, 2012

(54) BIOCOMPATIBLE DENATURED ALBUMIN LAMINA

(75) Inventors: Yasmin Wadia, Humble, TX (US); Scott Alan Prahl, Portland, OR (US)

(73) Assignee: Providence Health System - Oregon, Portland, OR (US)

(21) Appl. No.: 11/102,886

(22) Filed: Apr. 8, 2005

Related U.S. Patent Documents

Reissue of:
(64) Patent No.: 6,680,063
Issued: Jan. 20, 2004
Appl. No.: 09/686,594
Filed: Oct. 6, 2000

U.S. Applications:
(60) Provisional application No. 60/158,666, filed on Oct. 8, 1999.

(51) Int. Cl.
*A61K 9/00* (2006.01)
*A61B 17/08* (2006.01)

(52) U.S. Cl. ..... 424/402; 424/400; 424/422; 424/423; 424/424; 424/425; 424/426; 424/443; 600/8

(58) Field of Classification Search ..... 424/402, 424/400, 422–426, 443; 530/300; 600/8
See application file for complete search history.

(56) References Cited

U.S. PATENT DOCUMENTS

| | | | | |
|---|---|---|---|---|
| 5,156,613 | A | 10/1992 | Sawyer | |
| 5,201,745 | A | 4/1993 | Tayot et al. | |
| 5,209,776 | A * | 5/1993 | Bass et al. | 106/124.1 |
| 5,292,362 | A | 3/1994 | Bass et al. | |
| 5,713,891 | A | 2/1998 | Poppas | |
| 5,749,895 | A | 5/1998 | Sawyer et al. | |
| 5,929,044 | A | 7/1999 | Poppas | |
| 5,931,165 | A | 8/1999 | Reich et al. | |
| 6,110,212 | A | 8/2000 | Gregory | |
| 6,211,335 | B1 | 4/2001 | Owen | |
| 6,221,068 | B1 | 4/2001 | Fried | |
| 6,323,037 | B1 | 11/2001 | Lauto | |
| 6,372,228 | B1 * | 4/2002 | Gregory | 424/400 |
| 6,391,049 | B1 | 5/2002 | McNally | |
| 6,583,117 | B2 | 6/2003 | Owen | |
| 6,685,730 | B2 * | 2/2004 | West et al. | 607/89 |
| 6,921,412 | B1 | 7/2005 | Black | |

FOREIGN PATENT DOCUMENTS

WO WO 91/04073 4/1991

OTHER PUBLICATIONS

McNally et al, Lasers in Surgery and Medicine, 24, 319-331 (1999).*
Ma et al, Surface Science, 56, 117-125 (1976).*
L.S. Bass, M.D. and M.R. Treat, M.D.; Laser Tissue Welding: A Comprehensive Review of Current and Future Clinical Applications; *Lasers in Surgery and Medicine* 17:315 (1995).
Beatriz Farruggia, et al.; The Participation of Human Serum Albumin Domains in Chemical and Thermal Unfolding; *Journal of Protein Chemistry,* vol. 20, No. 2, 2001.
Karen M. McNally, et al.; Photothermal effects of laser tissue soldering; *Phys. Med. Biol.,* 44 (1999) 983-1002, Printed in the UK.
Thomas Menovsky, et al.; Laser Tissue Welding of Dura Mater and Peripheral Nerves: A Scanning Electron Microscopy Study; *Lasers in Surgery and Medicine* 19:152-158 (1996).
A. Luato, M.Sc., et al.; Laser Nerve Repair by Solid Protein Band Technique. I: Identification of Optimal Laser Dose, Power, and Solder Surface Area; *Microsurgery,* 18:55-59, 1998.
Dix P. Poppas, M.D., et al.; Human Albumin Solders for Clinical Application During Laser Tissue Welding; *Lasers in Surgery and Medicine* 19:2-8 (1996).
Andrew J. Kirsch, et al.; Skin Flap Closure by Dermal Laser Soldering: A Wound Healing Model for Sutureless Hypospadias Repair; *Urology* 50 (2), 1997.
Kazutomo Imahori; The Structure of Surface Denatured Serum Albumin Molecule; *Scientific Papers of the College of General Education, University of Tokyo,* vol. 1, No. 1, Oct. 1951.
G. Dapper, et al.; Attachment of Gelatin Films to Tissue Using Argon Beam Coagulator; *John Wiley & Sons, Inc.,* 1998.
Antonio Lauto, et al.; Laser Activated Solid Protein Bands for Peripheral Nerve Repair: An In Vivo Study; *Lasers in Surgery and Medicine* 21(2):134-41, Dec. 7, 1998.
Antonio Lauto; Laser Activated Protein Solder for Peripheral Nerve Repair, *Macquarie University,* Sydney, Australia; Master of Science Thesis, Mar. 1996.
Antonio Lauto, et al.; Laser Activated Solid Protein Bands for Peripheral Nerve Repair: an in Vivo Study; Dec. 7, 1998; Lasers in Surgery and Medicine 21(2):134-41, 1997.

(Continued)

*Primary Examiner* — T. D. Wessendorf
(74) *Attorney, Agent, or Firm* — Greenberg Traurig, LLP

(57) ABSTRACT

The present invention provides a denatured albumin lamina, useful for repairing lesions on solid visceral organs. The lamina comprises human serum albumin, formed into a thin, pliant sheet and denatured. The denatured lamina can be sterilized and stored until used. As well, it can be impregnated with a variety of bioagents. A method for repairing a lesion on a solid visceral organ includes applying an energy-absorbing proteinaceous material to a lesion site on the solid visceral organ lesion; irradiating the proteinaceous material with energy sufficient to fuse the energy-absorbing material at least partially to the lesion site; applying a biocompatible denatured albumin lamina onto the proteinaceous material on the lesion site; and irradiating the biocompatible albumin lamina and the proteinaceous material with energy sufficient to fuse the biocompatible albumin lamina to the proteinaceous material and/or the lesion site. A laser solder can be deployed beneath the lamina to aid in welding it to the organ surface using laser light energy.

18 Claims, 6 Drawing Sheets

OTHER PUBLICATIONS

Karen McNally; Optical and Thermal Studies of Laser Solder Tissue Repair In Vitro; Jul. 15, 1998; Macquarie University, Sydney, Australia; Ph.D. Thesis.

A. Lauto; Laser Activated Protein Solder for Peripheral Nerve Repair; Mar. 1996; Macquarie University, Sydney, Australia; Master of Science Thesis.

* cited by examiner

BIOCOMPATIBLE DENATURED ALBUMIN LAMINA

Matter enclosed in heavy brackets [ ] appears in the original patent but forms no part of this reissue specification; matter printed in italics indicates the additions made by reissue.

CROSS-REFERENCE TO RELATED APPLICATIONS

[This application claims priority from U.S. Ser. No. 60/158,666, filed Oct. 8, 1999, and incorporated by reference.]

*More than one reissue application has been filed for the reissue of U.S. Pat. No. 6,680,063, which originally issued Jan. 20, 2004, and claimed priority from, and incorporated by reference, U.S. application Ser. No. 60/158,666 filed Oct. 8, 1999.*

*These reissue applications are: U.S. reissue application Ser. No. 11/906,743, filed Oct. 4, 2007 which is a continuation reissue of U.S. reissue application Ser. No. 11/102,886, filed Apr. 8, 2005 (the present application), and divisional U.S. reissue application Ser. No. 11/454,180, filed on Jun. 15, 2006 (abandoned), which claims priority to reissue application Ser. No. 11/102,886.*

STATEMENT OF GOVERNMENT RIGHTS

This invention was made with the U.S. Government support under Grant Number DAMD17-96-1-6006, awarded by the Army Medical Research and Materiel Command. The U.S. Government has certain rights in the invention.

BACKGROUND OF THE INVENTION

The invention relates generally to biological tissue welding, and more specifically to repairing a lesion to a solid visceral organ. The invention also relates to manufacturing biocompatible albumin lamina suitable for use as a scaffold or patch in the repair of tissue of a solid visceral organ.

Solid visceral organs such as the liver, spleen and kidney have a soft parenchyma richly interspersed with vasculature and thinly protected by a delicate fibrous capsule with limited internal fibrous support. This structure makes such organs prone to fracture and laceration with blunt abdominal trauma. Such organs are also frequently injured following abdominal trauma. For example, the liver is the most commonly injured organ following abdominal trauma. It is the second most commonly injured following blunt injuries and the third most commonly injured in penetrating injuries.

Surgery of solid visceral organs like liver, spleen and kidney have always proved to be challenging, as these organs bleed profusely if traumatized and hold sutures rather poorly. Exsanguinating hemorrhage remains a significant cause of immediate mortality. A 3 cm parenchymal depth laceration has a 19% mortality and a parenchymal disruption involving 25-50% of a hepatic lobe has 28% mortality.

Few intra-abdominal injuries are as technically demanding as a major liver laceration. Such wounds require erudite judgment and innovative surgical techniques to prevent intraoperative exsanguination accelerated in some cases by hemodilution and coagulopathy. Conventional suture repair of major hepatic trauma additionally has a delayed morbidity and mortality from septicemia, peritonitis, biliary fistulae, and delayed intra-abdominal hemorrhage.

The current surgical armamentarium for liver lacerations is limited to mass ligation of the lacerated liver with absorbable sutures, omental wrapping, packing with re-exploration, mesh hepatorrhaphy, fibrin sealant and ultrasonic aspiration with argon beam coagulation. Suture repair of the liver frequently increases parenchymal damage and ischemic tissue loss. Packing can be complicated by persistent hemorrhage and/or abdominal compartment syndrome and requires re-exploration to remove the packing. Biliary fistula and abscess formation can also complicate this technique. These difficulties also arise in repairing lesions in the kidney and spleen. They also present an obstacle to surgical treatment of solid visceral organs, for example, excision of tumors.

The use of lasers alone to control hemorrhage in the liver has had limited success in the past. Tissue coagulation is the method of heating to denaturation the constituents of the tissue itself. Attempts at hemostasis using the $CO_2$ laser have failed to show significant benefit when compared to the diathermy. Other work showed that the $CO_2$ laser is ineffective at sealing vessels larger than 1 mm and that argon and Nd:YAG lasers are ineffective at stopping flow in vessels larger than 4.5 mm. These lasers achieve hemostasis by extensive (5-10 mm depth) thermal coagulation of proteins, causing major collateral tissue damage.

The use of laser energy to join tissue by heating a protein solder, typically albumin, is referred to as tissue welding. Laser soldering has been employed as an alternative to suture repair of injured tissues. Laser soldering was first utilized to anastomose rat ureters. Incorporating albumin solder into laser repairs was found to aid in controlling hemorrhage.

Solders are generally viscous liquids of biocompatible compositions. A representative composition is that of U.S. Pat. No. 5,292,362 (to Bass et al.), which discloses a liquid solder of collagen or albumin. Liquidity permits the solder to be easily applied and formed to the lesion, while its concentration serves to retain the solder at the applied site until irradiated. The highest viscosity of albumin readily producible corresponds to a 55-57% aqueous solution, enabling higher tensile strength weld joints. However, this albumin solder solution has the approximate consistency of honey. Higher concentrations of albumin, i.e., above 58%, dehydrate rapidly and cannot be freely handled in air.

It was recognized that adding a light-absorbing chromophore to the solder would increase and localize the absorption of energy to the solder level, thereby reducing both the amount of laser light required and collateral tissue damage. A chromophore is utilized to increase and localize the absorption of energy. The selection of chromophore also drives the choice of laser energy to be applied. For example, by using indocyanine green (ICG) as the exogenous chromophore, a diode laser could be operated at 800 nm. These lasers have the advantage of being relatively inexpensive. Further, their near-infrared light is poorly absorbed by solid visceral organ tissue, substantially mitigating thermal damage during a laser repair. Lastly, the specific absorption of energy by the chromophore pinpoints the heat generation locus to the solder layer. Reducing the amount of laser light required for solder activation permits lower laser energy settings. More efficient energy absorption also allows the use of pulsed lasers, further reducing collateral thermal damage during laser repairs.

Tissue welding using only an ICG-augmented albumin solder confers no advantage in some scenarios. Soldering can be employed to achieve hemostasis of severed liver venous sinusoids of larger diameters (i.e., 5 mm and above). However, the weld joints produced are brittle and of relatively low tensile strength. Previous repairs focus on nerve, ureter and vesicular and usually further include stay sutures. Solid visceral organs require a support contribution from the repair material. Solders exhibit low tensile strength and are not well-suited to provide this support. To date, laser soldering applications have not shown a clear benefit over conventional suture repair, and have not gained clinical acceptance Mechanical considerations also militate against effecting lesion repair with irradiated liquid solder. Welding liver requires the application of an ICG-doped albumin solution to the weld area. As the ICG absorbs the laser light energy, the amount of ICG present (e.g., the thickness of the applied solution) is a significant factor in weld success and duplication. The non-uniformity in the albumin layer thickness during tissue repair is currently the greatest source of variability in laser repair using albumin solder.

Blood, bile and other fluids routinely exude from lesions. During laser solder repair, this seepage displaces the liquid solder from the surface of the damaged organ. Because of its viscosity, liquid solders cannot easily be manipulated to regain contact with the lesion site, instead necessitating deposit of further solder material and/or exposure of the lesion to additional energy. Alternatively, the fluids are irradiated and/or trapped beneath the welded solder material. Such entrapped weld joint contaminants adversely affect joint quality, strength and durability.

Laser soldering alone is also suboptimal for the repair of resecting injuries to solid visceral organs. Satisfactory repair of raw surface lesions is typically obtained with folding of the tissue or the application of some sort of a supportive film, described below. In addition to its bond strength, laying down and irradiating an uneven solder cover is likely to produce thinner, weaker points in the tissue weld. The longevity of repairs of raw surface traumas using only liquid solder is therefore suspect.

Efforts have also been made to repair damage to nerves and small vessels using solid welding patches, such as Small pieces of dried albumin (1×3×0.5 mm strips). Further, such strips possess a low tensile strength, making them unsuitable for gross repairs such as resection or blunt trauma injuries. Lastly, these materials have been employed to repair nerves, ureters and other vessels. A need exists to direct the method of tissue welding to tissues possessing soft parenchyma, such as the liver, kidney and other solid visceral organs.

Solid biocompatible materials have been employed to repair injuries to tissues needing greater structural support than is offered by solder alone. Compositions include gelatin (U.S. Pat. No. 5,931,165 to Reich et al.); elastin (U.S. Pat. No. 6,110,212 to Gregory, et al.); and collagen (U.S. Pat. No. 5,749,895 to Sawyer et al.). Sawyer et al. teach making and using a sheet preferably made of collagen. The reference also mentions albumin as one of a number of alternative candidate materials. However, Sawyer et al. provide no description of the manufacture, method of use or physical characteristics of an albumin film. Further, none of the prior art references describe using an albumin film in the repair of injuries to solid visceral organs, such as liver, kidney and spleen.

Different methods have been attempted by Applicant to produce useful thin films of albumin. Prior efforts to extrude 55-57% albumin failed, as the solution would re-congeal upon exiting the extrusion orifice. Consequently, a need exists for a stable, pliable albumin lamina.

Applicant has experimented with welding liver lesions in liver by the application of ICG-doped liquid albumin solder to the weld area. As it is the ICG that absorbs the laser light energy, the thickness of the applied solution is a critical factor in weld success and repeatability. To date, this variable has not been controllable and the need for accurate and uniform albumin application persists. The albumin lamina of the present invention addresses this need by focusing on the preparation of thin albumin films, providing for the application of albumin of uniform and consistent thickness to a weld site.

Applications of energy to living tissue have the additional drawback of thermal damage to the lesion site under repair. The degree of damage varies according to the energy type and the amount applied, but can in some cases be substantial. In tissue coagulation, for example, the tissue is literally melted and then fused. An argon ion beam coagulator, used in this procedure, produces damage penetrating 3-4 mm into the tissue. While this repair technique seals the surface over an incision, superficial injury is sustained by the organ parenchyma well beyond the precise area of the incisive trauma. Such thermal damage also increases the risk of improper healing, spawning fistulae and other unwanted post-procedural complications. While thermal damage is more limited in soldering, a need exists to further minimize and control damage to healthy tissue surrounding or adjacent to a lesion in a locus of repair.

The present invention relates to the use of laser welding techniques on liver, kidney and spleen—solid tissues that are notoriously difficult to repair with sutures. Applicant's experimental efforts achieved rapid hemostasis of in vivo liver lacerations (10 cm long and 1 cm deep) and lobar resections (5 by 2 cm) in swine. However, an integral part of the success of the swine experiments was the use of the pig's omentum as a welding patch. A piece of the omentum was harvested during the procedure and placed over albumin-ICG solder. The omentum was then welded to the liver. Due to its transparent nature, the omentum let nearly 100% of the laser energy pass through and a strong weld occurred. The omentum thus served successfully as a hemostatic patch, reinforcing the albumin solder.

Successes with pig omentum could not be translated directly to humans, however. Native porcine omentum cannot be implanted in humans. On the other hand, human omentum is fatty and opaque, unlike the pig omentum. Therefore, rather than transmitting nearly all the laser energy, human omentum scatters a considerable amount, making it difficult to weld human omentum to tissue.

SUMMARY OF THE INVENTION

With this in mind, an albumin patch according to the present invention was developed which transmits 90% of incident laser energy. Being composed of albumin, the patch forms a strong bond with liquid albumin solder. Though not as strong a weld as those using omentum, the patch provided significant reinforcement to the weld site. Using the albumin lamina material provides substantially greater weld strength than solder alone.

The present invention provides a denatured albumin lamina, useful for repairing lesions on solid visceral organs. The lamina comprises human serum albumin, formed into a thin, pliant sheet and denatured. The denatured lamina can be sterilized and stored until used. As well, it can be impregnated with a variety of bioagents. Its mechanical properties make it especially suitable for use in tissue welding on solid visceral organs.

In another aspect of the present invention, a method is provided for manufacturing the denatured albumin lamina. The method comprises placing a quantity of viscous albumin solution between two nonporous sheets, then spreading the albumin solution between the sheets to a selected and substantially uniform thickness. The albumin solution sandwich is thus formed is placed into a container, which is then evacuated. The sandwich is then heated, by autoclaving or immersion in a water bath of at least 86° C. Denaturation of the entrapped albumin solution changes its state from a viscous liquid to a flexible solid.

Another aspect of the present invention is a method for using the albumin lamina according to the present invention to repair a lesion on a solid visceral organ. The method comprises welding the albumin lamina over a lesion on a solid visceral organ. A laser solder is deployed beneath the lamina to weld it to the organ surface. In alternative embodiments, the albumin lamina is produced with additives in the form of bio-active agents.

Further details and advantages of the present invention will be apparent from the following detailed description, in conjunction with the accompanying drawings.

DETAILED DESCRIPTION

As used hereinafter, the terms "percent" and "%" refer to weight per volume (gm/100 dl) unless otherwise noted.

The albumin lamina of the present invention is made from FDA-approved human serum albumin. It is therefore completely biocompatible and biodegradable. Typically, other biomaterials (gelatin, collagen or elastin) are culled from animal sources. These materials engender attendant concerns about antigenicity, immune rejection and foreign body reactions. Furthermore, transmission of animal viruses and diseases is a concern. Use of human serum albumin substantially mitigates these concerns, as the protein sequence and structure vary little between individuals. As well, human serum albumin is amenable to sterilization and obviates the risk of animal diseases crossing species barriers into humans.

Figure 1:
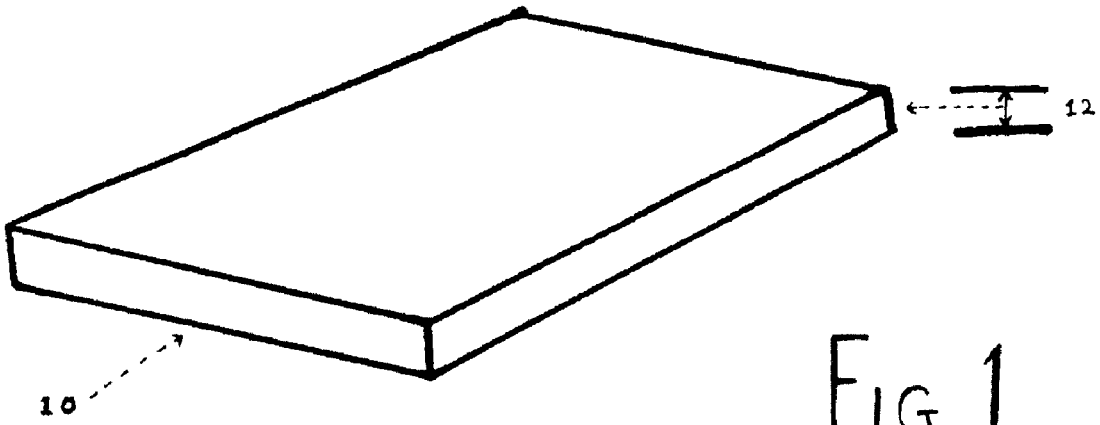
FIG. 1 is a physical representation of an albumin lamina according to the present invention.

A typical lamina 10, shown in FIG. 1, is a film having a predetermined thickness. The preferable thickness is 200 μm, although the lamina can be manufactured to greater or lesser thicknesses in a range of 75 μm to greater than 300 μm. A denatured albumin lamina is clear, thin, flexible and preferably of uniform thickness. It can be manipulated by hand easily and without special care, due to its sufficiently high tensile strength and pliability. Although possessive of slight tackiness, it does not bond or stick to itself.

The denaturation leaves the lamina stable in a variety of environments. The denatured albumin lamina will not solubilize in water or saline solution or after contact with tissue. The denatured albumin lamina of the present invention is also stable in air. The denatured lamina requires vacuum storage but maintains its pliancy for as long as approximately 15 minutes on the benchtop.

Several advantages are provided by the denatured albumin lamina patch in tissue welding over the prior art. First, its relative insolubility enables the user to reposition the lamina after placement on a lesion site. In contrast to prior welding patch materials, the denatured albumin lamina can be glided over the organ surface. Furthermore, the denatured lamina can be picked up for removal or repositioning.

Second, the lamina results in a welded albumin layer of uniform thickness because of its consistent dimensions. This uniformity eliminates weak spots in the tissue weld, caused by thin areas in the soldering or welding materials.

Third, the lamina can be impregnated with one or more bioactive agents, comprising pharmaceuticals, hormones, hemostatic agents, or other therapeutic agents. Spot-welding the lamina to the lesion site avoids irradiation of the entirety of the lamina, preserving such compounds during the welding process. Compounds can be selected which are not damaged by the particular energy type used in the welding method.

Fourth, the denatured albumin lamina can be sterilized by autoclaving or gamma irradiation. Because denaturation is desired, autoclaving can accomplish both the sterilization and denaturation steps in the manufacture of the lamina.

A study was done of albumin lamina cured at 100° C. for 30, 60,120, 200, 300, and 600 seconds in which a dog bone die was used to cut the albumin strips so that the failure point was consistently in the middle of the sample, rather than at the clamps. Strips of approximately 2×1 cm were pulled in a Chatillon Materials Tester. Ultimate strength was calculated by dividing the cross-sectional area of the test strip into the force required to break the test strip.

Figure 2:
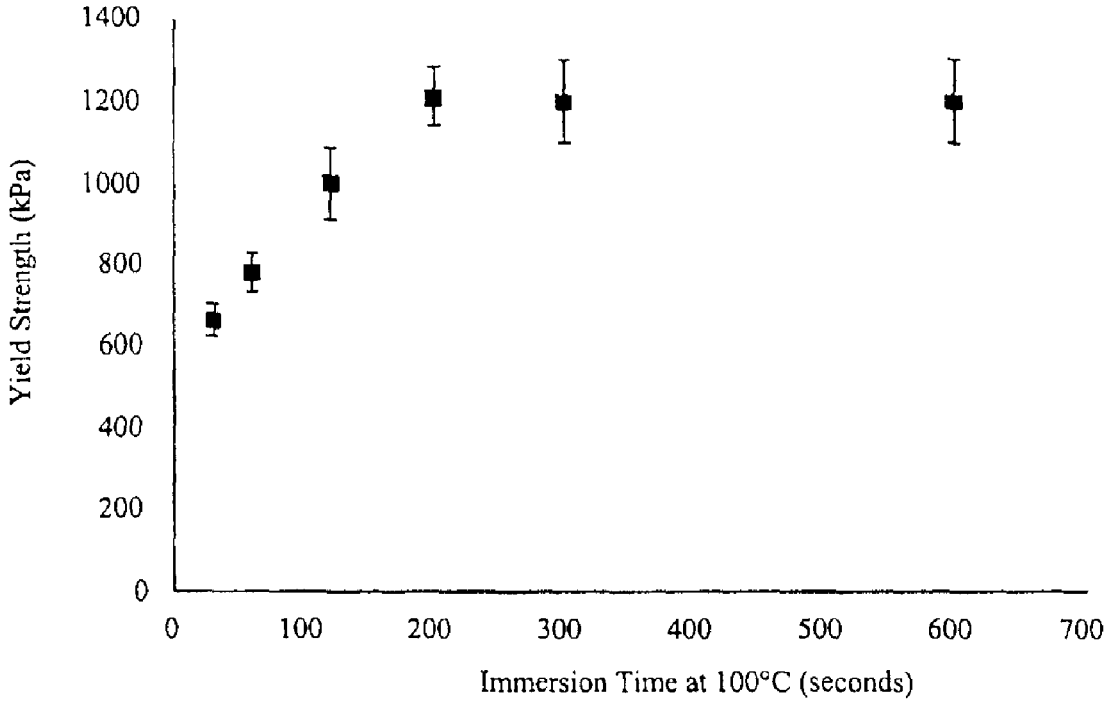
FIG. 2 is a scatter-plot of ultimate strength data for one embodiment of the lamina of FIG. 1.

Ultimate strength results are shown in FIG. 2. The ultimate strengths were recorded along with the exact width and thickness of each sample. The ultimate strength was calculated by dividing the force required to break the sample by the cross-sectional area (width×thickness).

Ultimate strength is seen in FIG. 2 to increase almost linearly up until 200 seconds, after which strengths vary only trivially. The data indicate that there may be a strength increase in the sheet, if it is cured at temperatures exceeding 95° C.

Figure 3:
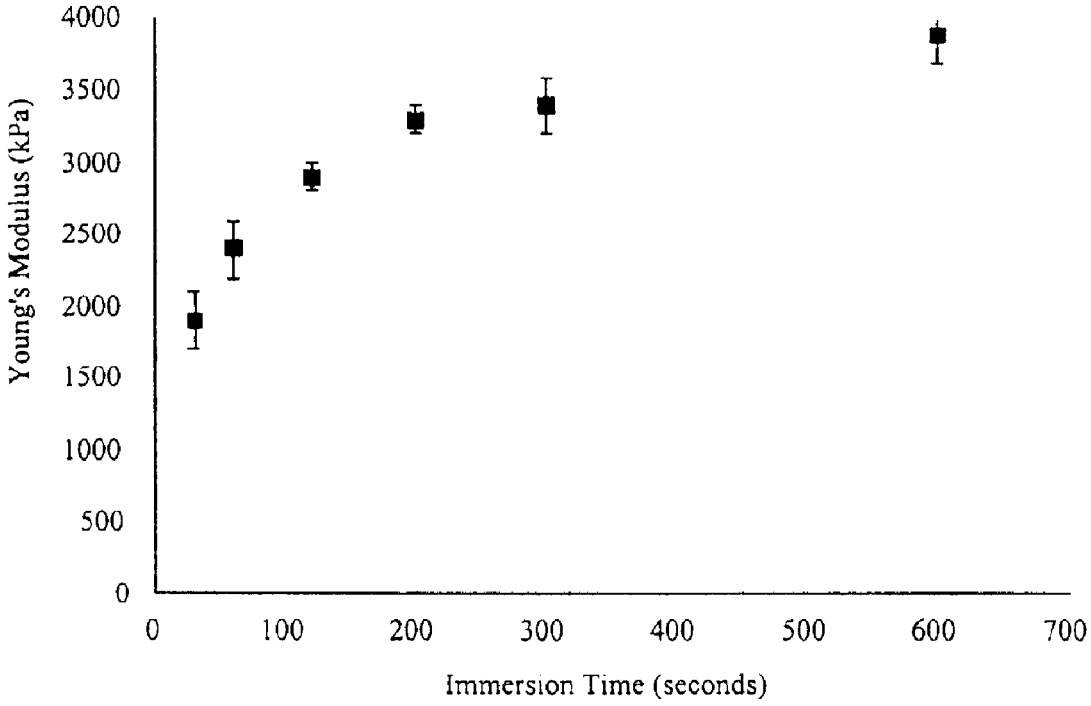
FIG. 3 is a scatter-plot of elasticity data for one embodiment of the lamina of FIG. 1.

FIG. 3 shows the elasticity of albumin strips denatured at 100° C. Young's modulus of elasticity was calculated for each sample by a linear fit of stress/strain data for strains ranging from 0 to 0.1. For denatured albumin strips cured at 100° C., the stiffness (Young's modulus) increases with increasing curing time, with the most increase occurring in the first 200 seconds.

Figure 4:
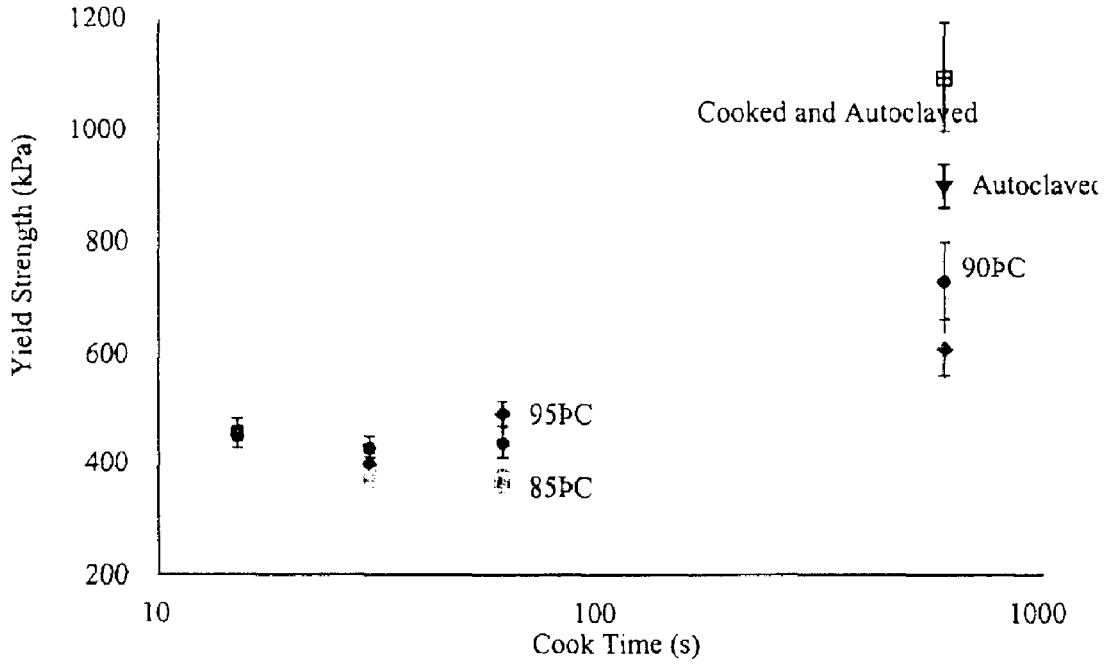
FIG. 4 is a scatter-plot of ultimate strength data as a function of curing temperature, curing time and curing method in the manufacture of lamina according to one aspect of the present invention.

FIG. 4 shows the ultimate strengths in kilopascals for albumin strips denatured by heat bath immersion at 85° C., 90° C. and 95° C. As well, the effects were assessed of heating by autoclaving at 110° C., with and without a brief (15-30 second) heat bath immersion prior to autoclaving.

There is an increase in strength in the 600 second data over the shorter cure times. However, there is no significant change in strength between 15 second and 60 second curing times. Moreover, there is no significant difference in strength between the three different temperatures tested.

Elasticity was also influenced by boiling time. Boiling for periods beyond 200 seconds had only a minor impact on lamina elasticity.

Overall, temperatures of at least 90° C. are needed to achieve strips with an acceptable ultimate strength. Only a marginal increase in both ultimate strength and elasticity was imparted by boiling in excess of 200 seconds.

The denatured albumin lamina of the present invention has varied applications. It can be employed as a substrate for temporary external integument replacement in burn treatment or other areas of extensive tissue loss. In this use, the capacity of the lamina to be impregnated with antibiotics or other bioagents is particularly beneficial. Alternatively, the lamina may be manufactured with substantial structure in all three dimensions. A lamina so cast is useful as a scaffolding, for example, in the tissue-engineering of organs.

To make denatured albumin lamina according to the present invention, a liquid albumin solution of approximately 53% to 57% is utilized. In a preferred embodiment, the albumin solution is concentrated to 53-55%.

Figure 5:
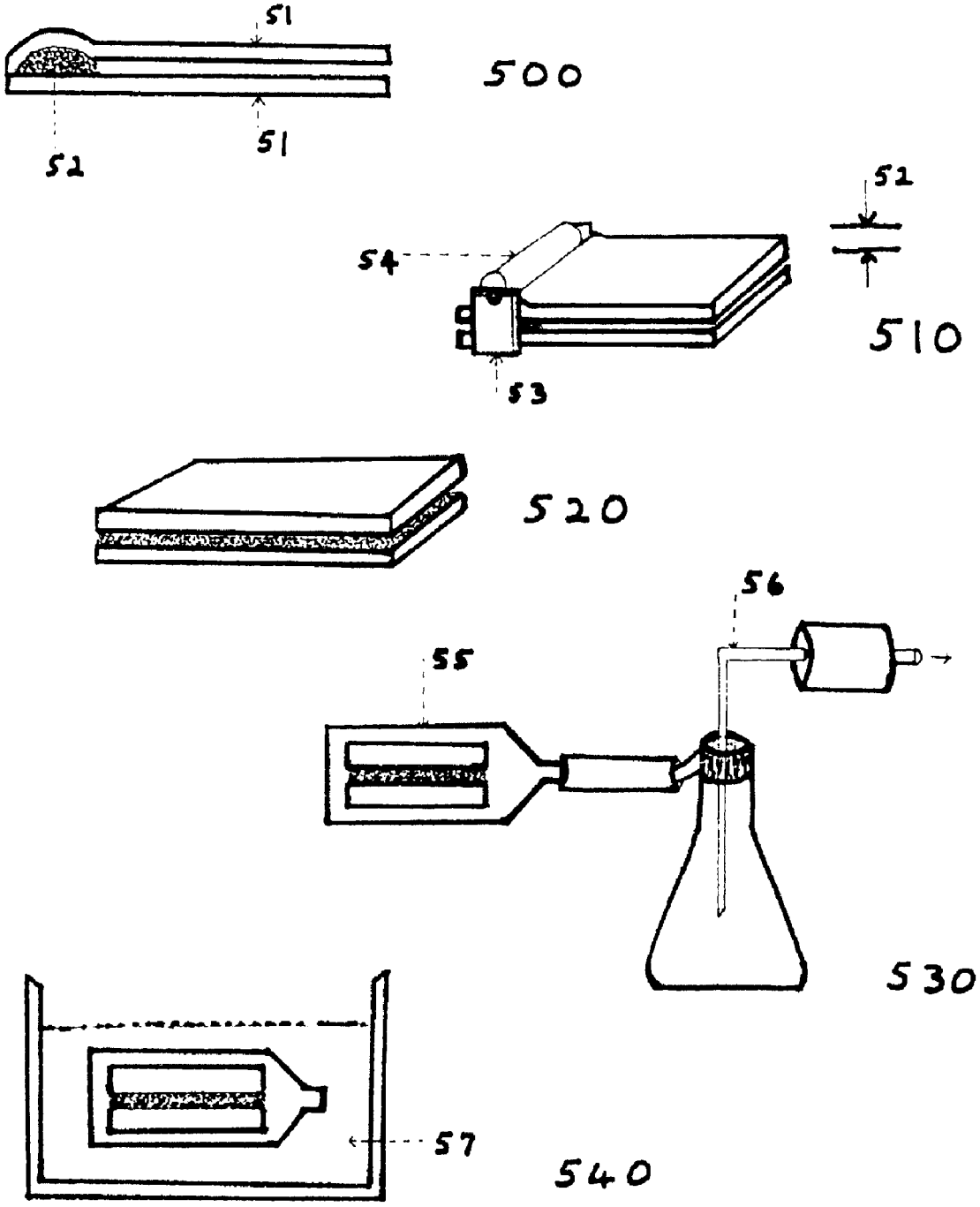
FIG. 5 shows a method of making a denatured albumin lamina according to one embodiment of the invention.

FIG. 5 shows a method of making denatured albumin lamina. In a first step 500, the concentrated albumin 52 is placed between two nonporous sheets 51, e.g., the main panels of a Kapak bag plastic. Typically, approximately 1 cc of albumin solution is placed between the edges of the two aligned plastic sheets. These sheets are then placed in another Kapak bag 55 (not shown in steps 510 and 520 for clarity) and the entire unit rolled 510 through a rolling mill 53, forward and backward, to spread the albumin evenly 520 and to a uniform thickness 52. The roller 54 height can be calibrated using known thickness of materials placed between the rollers. After rolling, the outer bag is evacuated 530, i.e., with a vacuum pump/trap 56, and the open edge heat-sealed (not shown).

At this point, the entire package is placed 540 in a hot water bath 57 of controlled temperature to denature the albumin. During the heating step, the albumin protein is denatured. It is believed that the molecules interact and form a polymer upon cooling.

Alternatively, sheets are cured at 90° C. for 15 seconds and then autoclaved at 110° C. for 10 minutes. In yet another embodiment, albumin lamina is denatured by autoclaving only.

The factors most greatly impacting the properties of the resultant denatured albumin lamina are serum albumin solution concentration (50-57%), curing temperature (86-120° C.), curing time (15 seconds to 10 minutes) and curing pressure (1-3 atm).

The denatured albumin lamina are typically double-packaged and stored to prevent dehydration and maintain pliancy. While so stored, the lamina can be gamma-irradiated (25-35 Gy) to sterilize the biomaterial and container.

A method of using the denatured albumin lamina of the present invention in the repair of lesions on solid visceral organs is herein disclosed. Efficacy has been assessed directly in benchtop experiments.

Figure 6:
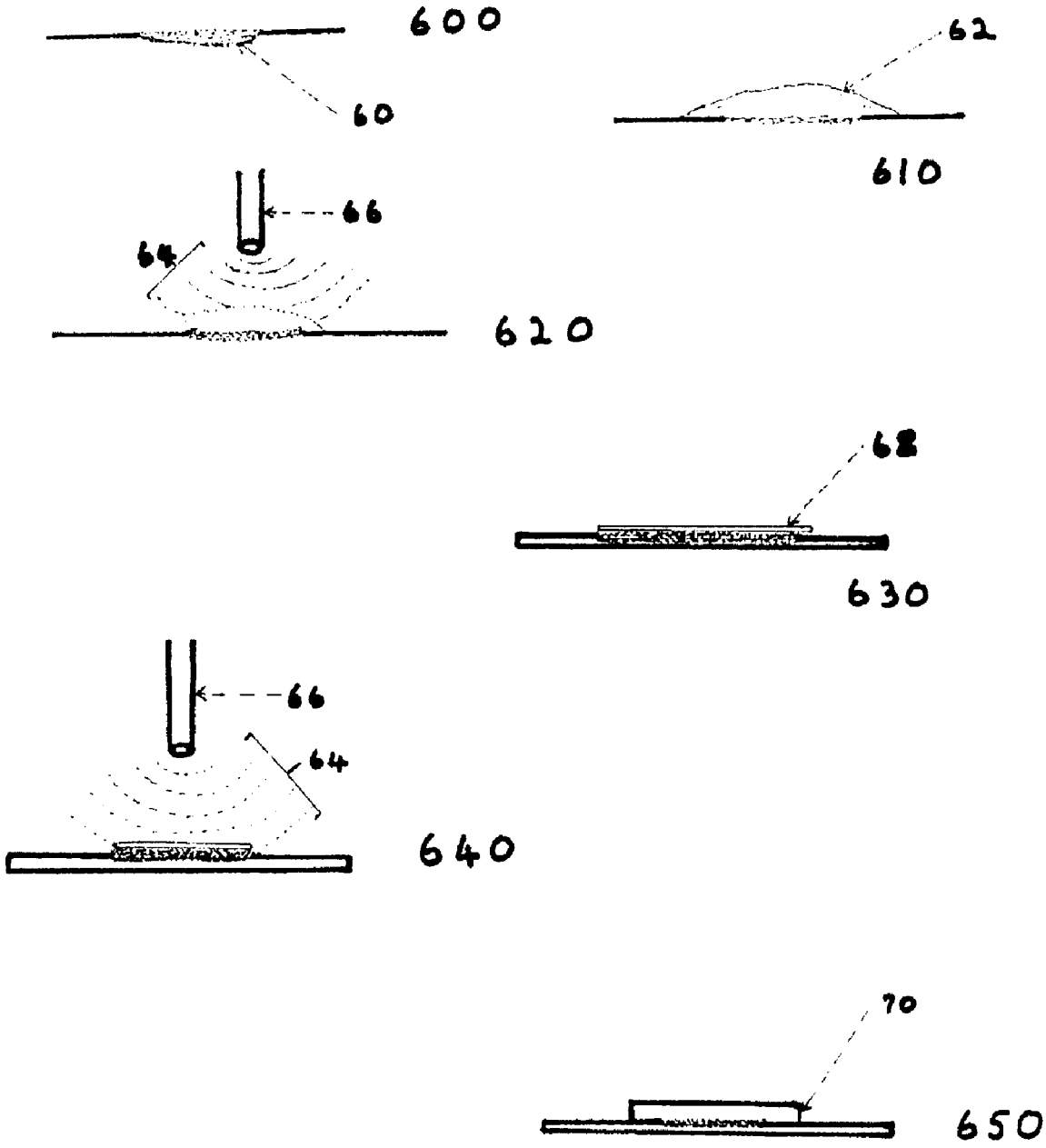
FIG. 6 shows a method of repairing a lesion to a solid visceral organ surface using a denatured albumin lamina according to one embodiment of the invention.

As illustrated in FIG. 6, a lesion 60 on a solid visceral organ can be repaired using the denatured albumin lamina of the present invention. The repair begins with the application to the lesion site of a quantity of an energy-absorbing material 62. One such material is liquid albumin solution (solder) doped with a chromophore. In a preferred embodiment, solder of 53% to 55% albumin is used, further containing ICG at a concentration of approximately 0.1 mg/ml.

The lesion site is then irradiated 620 with energy 64 from an energy source 66. Because the solder is energy-absorbing, it denatures. Surface tissue in contact with the solder also heats and denatures. With sufficient energy irradiation, fusion of sinusoids results in substantial hemostasis at the lesion site. In in vivo applications, this step serves to achieve substantial hemostasis at the lesion site. While hemostasis is not necessary for the subsequent laminar welding with high strength, hemostasis is a desired consequence of the lesion repair. Blood loss is thereby further minimized and the lesion more efficaciously treated.

A denatured albumin lamina 68 according to the present invention is then placed 630 over the welded energy-absorbing material 62 on the lesion site 60. Alternatively, the lamina is first trimmed to roughly conform to the particular dimensions of the lesion.

The lesion site is then again irradiated 640 with energy 64 from an energy source 66. The lamina, being transparent to the laser light at the chosen wavelength, absorbs little light energy and hence heats minimally as compared to the solder. The energy-absorbing material beneath the lamina absorbs energy and heats, conducting heat to the lamina. With sufficient energy irradiation, the albumin solder and the denatured albumin lamina are denatured at the protein level. It is believed that the albumin molecules intertwine with one another and with tissue. Upon cooling, the lesion site is weld-sealed, wherein the denatured albumin lamina and the lesion site are welded together.

In the benchtop experiments, lacerating lesions were made to the surface of a porcine liver. Reinforcement by an albumin lamina gives hepatic lesion repairs a measured continuity and prevents accidental de-lamination of the soldered albumin from the liver. The albumin lamina also increases the welded surface area, holding the lacerated edges together much like an integumentary bandage across cut skin edges.

In a preferred embodiment, the lesion site is irradiated 620 with energy 64 after the deposition 610 of solder 62 and before the placement thereon 630 of the denatured albumin lamina 68.

In liver surgery, rapid hemostasis in presence of coagulation failure may be necessary. Hepatic lesion repair, performed according to a less preferred embodiment of the current method, achieved complete hemostasis at a rate of about 9.4 sec/cm$^2$. This modality effectively seals the liver surface and joins lacerations with minimal thermal injury. Further, the present method works independently of the patient's coagulation status.

FEATURES AND BENEFITS

The successful treatment of lesions using denatured albumin lamina and a laser offers a new modality of treatment of lesions in the liver and other solid visceral organs of humans. Conventional suture repair of the liver is strongly influenced by the skill of the surgeon. In contrast, the low pressure portal vein and hepatic vein make the liver suitable for tissue welding. It is relatively simple to repair an injured liver effectively using the present invention, primarily because of the visual change in the albumin solder as it is irradiated. This allows one to recognize when a sufficient number of laser pulses have been delivered.

One drawback to tissue welding is that a dry operating field is needed, necessitating Pringle's maneuver perform the procedure. Therefore, for grade IV and V liver trauma repair, total hepatic isolation may be required. The ten minutes required to complete a laser repair of the liver is well within ischemic time tolerated by the liver. The time required for tissue welding is comparable to suture repair. This time can be shortened by using larger laser spot sizes with correspondingly higher laser pulse energies. Another advantage of laser soldering is that the 800 nm laser energy is selectively absorbed by ICG dye; accidental misdirection of the laser beam at the energy levels used had no effect on the surrounding viscera. More rapid repairs may be dictated by those patients presenting with other critical injuries; i.e., extensive trauma or injuries to numerous body sites.

A benefit of the present invention is its mitigation of collateral damage inflicted upon the tissue during repair. The damage sustained by the liver in the above examples was significantly less for tissue weld repairs (typically 0.5-1.0 mm) than the 1 cm ischemic region seen in the conventional suture repair. During tissue welding, thermal damage is confined primarily to the albumin on the surface, with some heating of the surface of the liver caused by heat conduction. This depth of damage is about an order of magnitude smaller than that of other techniques that rely on thermal coagulation of parenchyma to achieve hemostasis (e.g., electrocoagulation, argon ion beam coagulation, and focused ultrasound). Even suture repair is accompanied by a significant layer of ischemic parenchyma that may eventually become necrotic with attendant complications.

The denatured albumin lamina are stable and retain their transparent quality even when heated to the high temperatures of 80° C. to 120° C. that are required for laser welding. The lamina needs to be energy-transparent at these temperatures so that the laser light reaches the albumin-ICG solder interface unrestricted. Collagen and other protein scaffold materials denature at 60° C. They also cloud over and restrict laser light penetration. Small intestinal submucosa, peritoneum and pericardium—all transparent collagen biomaterials—curl, shrink and coagulate when used in tissue welding.

Tissue welding can reduce the morbidity and mortality associated with bleeding, biliary leakage, and sepsis following liver surgery. The direct resection of invading tumors, primary hepatomas or other neoplasms buried deep within the parenchyma is therefore feasible. This resection is possible because the remaining raw organ surfaces could be welded with the albumin patch according to the present invention. Further, major hepatic resection for trauma or malignancy need no longer be done along anatomical planes. Patch welding enables resection of damaged or diseased liver along non-anatomical planes, thereby simplifying surgery and preserving hepatic parenchyma. Finally, patch welding can be translated without undue experimentation to the repair of other solid visceral organs such as the spleen and kidney.

Because it does not use endogenous coagulation pathways for hemostasis the method of organ repair according to the present invention holds promise for repair of solid visceral organ trauma even in the presence of coagulation failure or heparin. Experimental animals were given a single dose of heparin to imitate the coagulopathy that is usually seen in liver trauma.

Tissue welding is safe, quick and reliable in the presence of heparin. Repairs of porcine liver injuries using a method according to the present invention were straight-forward and resulted in small volumes of parenchymal damage. This technique can potentially reduce the morbidity and mortality associated with liver trauma and injury.

The lesion repair method of the present invention can be performed in conventional open surgical procedures, i.e. where access to internal body tissues and/or organs is achieved through a relatively large percutaneous surgical incision permitting laminar placement and exposure of the tissue/lamina to energy. The albumin lamina of the present invention can thus be introduced by the surgeon while directly viewing the target region and manipulating the lamina through the incision. Alternatively, the method of the present invention for welding tissue can be performed via less invasive surgical events, e.g., by laparoscopy, thoracoscopy, arthroscopy, or the like. Such procedures typically rely on creating small percutaneous penetrations and accessing the target region through cannulas placed within such penetrations. The target region is viewed through an associated viewing scope. In both open surgical procedures and less invasive procedures, the lamina will typically be trimmed to desired dimensions and configuration prior to placement on the tissue.

A person skilled in the art will be able to practice the present invention in view of the present description, where numerous details have been set forth in order to provide a more thorough understanding of the invention. In other instances, well-known features have not been described in detail in order not to obscure unnecessarily the invention.

Having described and illustrated the principles of the invention in a preferred embodiment thereof, it should be apparent that the invention can be modified in arrangement and detail without departing from such principles. All modifications and variations are claimed which come within the spirit and scope of the following claims.

What is claimed is:

1. A method of repairing a lesion on a solid visceral organ, comprising:

applying an energy-absorbing proteinaceous *solder* material to a lesion site on the solid visceral organ lesion;

irradiating the proteinaceous material with energy sufficient to fuse the energy-absorbing material at least partially to the lesion site;

applying a *scaffold comprising a* biocompatible denatured albumin lamina onto the proteinaceous material on the lesion site; and

*subsequent to applying the biocompatible denatured albumin lamina onto the proteinaceous material,* irradiating the biocompatible *denatured* albumin lamina and the proteinaceous material with energy sufficient to fuse the biocompatible *denatured* albumin lamina to the proteinaceous material [and&or] *and/or* the lesion site.

2. The method of claim 1, wherein the biocompatible albumin lamina is irradiated sufficiently to reduce hemorrhage at the lesion site by at least 50%.

3. The method of claim 1, wherein the biocompatible denatured albumin lamina has an albumin concentration of [about] *above* 50% to [58%] *57% prior to being manufactured into a denatured albumin lamina*.

4. The method of claim 1, further comprising:

clamping off blood supply to the lesion site of the solid visceral organ.

5. The method of claim 1, wherein the proteinaceous *solder* material is fluidic and is applied to a thickness of 100-1000 μm.

6. The method of claim 1, wherein the energy-absorbing material comprises a chromophore and the energy is light energy of a wavelength absorbed by the chromophore to fuse the biocompatible albumin lamina to the lesion site.

7. The method of claim 6, wherein the biocompatible albumin lamina is translucent to light energy.

8. The method of claim 5, wherein the proteinaceous material is fluidic and is applied to a thickness of 100-250 μm.

9. The method of claim 1 wherein the biocompatible denatured albumin [la] *lamina* contains sufficient water content to be pliable and has a thickness in a range of 75 μm to 300 μm.

10. The method of claim 8 wherein the albumin lamina has a thickness of about 250 μm.

11. The method of claim 1 wherein the albumin lamina has a tensile strength of at least about 625 kPa.

12. The method of claim 1 wherein the albumin lamina has an elasticity of about 1700 kPa to 4000 kPa.

13. The method of claim 1 wherein the albumin lamina contains a chromophore.

14. The method of claim 6 wherein the chromophore is indocyanine green.

15. The method of claim 1 wherein the albumin lamina contains at least one biologically active agent.

16. The method of claim 1, wherein the biocompatible albumin lamina is irradiated sufficiently to reduce hemorrhage at the lesion site by 50-90%.

17. The method of claim 1, wherein the biocompatible denatured albumin lamina comprises human serum albumin formed into a thin, pliant sheet *prior to being manufactured into a denatured albumin lamina*.

*18. The method of claim 3, wherein the biocompatible denatured albumin lamina has an albumin concentration in the range from 53% to 55% prior to being manufactured into a denatured albumin lamina.*

* * * * *